(12) United States Patent
Bedell et al.

(10) Patent No.: US 6,875,982 B2
(45) Date of Patent: Apr. 5, 2005

(54) ELECTRON MICROSCOPE MAGNIFICATION STANDARD PROVIDING PRECISE CALIBRATION IN THE MAGNIFICATION RANGE 5000X-2000,000X

(75) Inventors: Stephen W. Bedell, Wappingers Falls, NY (US); John Bruley, Poughkeepsie, NY (US); Anthony G. Domenicucci, New Paltz, NY (US); Devendra K. Sadana, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/604,989

(22) Filed: Aug. 29, 2003

(65) Prior Publication Data

US 2005/0045819 A1 Mar. 3, 2005

(51) Int. Cl.⁷ .......................... G01N 23/04; H01J 37/26
(52) U.S. Cl. .................. 250/307; 250/311; 250/252.1
(58) Field of Search ............................. 250/307, 311, 250/252.1

(56) References Cited

U.S. PATENT DOCUMENTS 4,068,381 A  *  1/1978  Ballard et al. .............. 250/311
5,744,800 A  *  4/1998  Kakibayashi et al. ....... 250/311
6,231,668 B1 *  5/2001  Loesch et al. ............... 117/89

\* cited by examiner

*Primary Examiner*—Jack I. Berman
(74) *Attorney, Agent, or Firm*—DeLio & Peterson, LLC; Kelly M. Reynolds; Lisa J. Jaklitsch

(57) ABSTRACT

A method and calibration standard for fabricating on a single substrate a series of crystalline pairs such that the d-spacing difference between the pairs will generate Moire fringes of the correct spacings to optimally calibrate the magnification settings of an electron microscope over a variety of magnification settings in the range of 5000× to 200,000×. The invention enables the tailoring of Moire fringe spacings to a desired magnification setting for calibration purposes by fabricating a series of patterns on a single substrate whereby each magnification setting is easily calibrated using a specific SGOI structure that is selected by a simple x-y translation across the top plan surface of the SGOI structure, therein eliminating the need for removing calibration samples in and out of the electron microscope. The method and calibration standard may be used for calibrating electron microscopes, such as, scanning transmission electron microscopes and transmission electron microscopes.

20 Claims, 5 Drawing Sheets

$$x_{SGOI} = \frac{(LWt_{SiGe}x_{SiGe})}{(L-0.9t_{Ox})(W-0.9t_{Ox})(t_{Total}-0.45t_{Ox})}$$

ELECTRON MICROSCOPE MAGNIFICATION STANDARD PROVIDING PRECISE CALIBRATION IN THE MAGNIFICATION RANGE 5000X-2000,000X

BACKGROUND OF INVENTION

1. Field of the Invention

The present invention is directed to a method of calibrating an analytical tool, and more specifically, to a method of calibrating electron microscopes for precise calibration of low to medium magnification ranges.

2. Description of Related Art

Electron microscopes, such as, transmission electron microscopes (TEM), are commonly used in the process of fabricating integrated circuits. TEMs are used to microscopically examine portions of a semiconductor die to determine the results of new or conventional processes. The examination may be to confirm the results of an experimental process, to determine the nature of a particular failure or defect in a semiconductor device, or even to find impurities within the semiconductor device. Of course, because of the nature of integrated circuits, the examination must often be performed on samples cut from the die in question.

The step of examining a semiconductor wafer for defects and structures is crucial in semiconductor fabrication as certain defects typically cause semiconductor device failure. In examining the semiconductor wafer using TEM, the wafer is removed from the production line and brought to an analytical tool for analysis. However, prior to inspection, the TEM tool must be calibrated to accurately and effectively inspect the semiconductor wafer for microstructural information.

Calibration of a TEM tool can be accomplished by a variety of known techniques. The most common calibration techniques for TEM processing include in-situ calibration and permanent calibration.

In-situ TEM calibration techniques require having a feature on the sample to be analyzed whereby the size and/or geometry of such feature are precisely known. As the exact feature size to be analyzed must be known, in-situ calibration is typically used for high magnifications, i.e., those magnifications greater than 200,000×, where the crystalline lattice spacings can be imaged. In those low to medium magnifications, i.e., those having magnifications ranging from 5000× to 200,000×, in-situ calibration is rarely used as the features to be analyzed by TEM are significantly smaller, and as such, the exact sizes and/or geometries of such features are not exactly known.

With low to medium magnifications, permanent TEM calibration techniques are typically performed on the TEM tool. In so doing, these low to medium magnifications of the tool are calibrated using "standards" having features of known sizes, geometries and/or thicknesses, either in plan view or cross sectional view. However, a disadvantage of permanently calibrating the TEM tool using standards is that such standards must have a wide range of these known features that match the fields of view for the magnification settings in question. A further disadvantage is that the standards typically must be removed from the TEM tool and rotated for calibration of such TEM tool in the X and Y directions. Another disadvantage of permanent calibration techniques is that they require measuring feature edges of the sample be analyzed, which, are often ill defined and introduce error into the calibration. Thus, as the edges of current and future generations of semiconductors continue to diminish in size, permanent calibration is inefficient as medium to high range magnification settings are required for analyzing these smaller edges.

Another permanent TEM calibration technique includes superimposing two crystalline materials, having known lattice spacings, to derive a Moire fringe pattern. This pattern is then used as a calibration "ruler." This technique enables the use of the entire field of view for calibration, yet, it only provides precise calibration for magnification settings whose field of view encompasses a significant number of Moire fringes, which is dependent on the two crystalline materials chosen. Further, the relative orientation between the two materials must be exactly known so that the Moire fringe spacing can be analyzed to high precision. As such, a variety of different precisely oriented crystalline pairs must be used to calibrate the entire magnification range from 5,000× to 200,000×.

It would be advantageous to have an analytical calibration technique that calibrates, to a high precision, a variety of magnifications over a wide range, particularly magnifications ranging from 5,000× to 200,000×, using a single calibration standard.

Therefore, a need continues to exist in the art for improved techniques and systems for calibrating analytical tools, particularly electron microscopy tools, which enable the use of a single sample to determine magnification over a medium to high magnification range, particularly 5,000× to 200,000×, in addition to providing a "ruler" which fills the entire field of view for each of a variety of selected magnification settings on such single sample.

SUMMARY OF INVENTION

Bearing in mind the problems and deficiencies of the prior art, it is therefore an object of the present invention to provide a technique and standard for calibrating analytical tools that enable the use of a single sample over a medium to high magnification range in addition to providing a "ruler" that fills the entire field for each of the selected magnification settings.

It is another object of the present invention to provide a technique and standard for calibration of medium to high magnification ranges of an electron microscope, particularly those magnifications ranging from about 5000× to about 200,000×.

A further object of the invention is to provide a technique and standard that allows two-dimensional (X and Y) magnification calibration over an entire field of view of a variety of selected magnification settings without removing the standard sample from the tool.

Still other objects and advantages of the invention will in part be obvious and will in part be apparent from the specification.

The above and other objects and advantages, which will be apparent to one of skill in the art, are achieved in the present invention, which, is directed to in a first aspect a method for forming an electron microscopy calibration standard on a single structure. The method includes providing a single substrate having at least a first layer and a second layer in lattice alignment. A material of a transformation layer is deposited over the second layer and then a plurality of differing sized bi-layer stacks are formed therein, whereby each bi-layer stack comprises the second layer and the transformation layer. Each of the plurality of bi-layer stacks are then modified so as to transform the second layer into a plurality of differing sized island structures with varying lattice parameters, therein providing a pattern of varying sized features with varying lattice parameters on the single substrate. The island structures comprise the material of the transformation layer. An electron microscopy calibration standard is then fabricated using the pattern of the varying sized features on the single sample.

The method may further include separating the first and second layers with a buried amorphous layer, whereby the buried amorphous layer mechanically decouples the first layer from the plurality of differing sized island structures. Preferably the first and second layers comprise a first silicon layer and a second silicon layer in lattice alignment, while the third layer comprises grown oxide and the transformation layer comprises SiGe. Each of the plurality of differing sized island structures with varying lattice parameters comprises a single crystal feature. The electron microscopy calibration standard may be a scanning transmission electron microscope calibration standard or a transmission electron microscope calibration standard.

In the invention, the buried amorphous layer may be a grown oxide layer which is grown at an elevated temperature to enable the transformation of the second layer within each of the differing sized bi-layer stacks into the plurality of differing sized island structures with varying lattice parameters. This elevated temperature ranges from about 1000° C. to about 1320° C.

Further in the invention, the pattern of varying sized features with varying lattice parameters on the single sample may be determined using a Moire fringe spacing that covers each of a magnification setting across a range of magnification settings for the electron microscopy calibration standard to be fabricated from the single sample. This range of magnification settings ranges from 5000× to 200,000×.

In a second aspect, the invention is directed to a method for calibrating an electron microscope. The method includes providing an electron microscope having a range of magnification settings, and then providing a single substrate having at least a first layer and a second layer in lattice alignment. A material of a transformation layer is deposited over the second layer and then a plurality of Moire fringe spacings that cover each magnification setting across the range of magnification settings for the electron microscope are determined. A plurality of differing sized bi-layer stacks of the second and transformation layers are then formed across the single substrate based on the plurality of Moire fringe spacings. Each of the plurality of bi-layer stacks are modified so as to transform the second layer within each of the differing sized bi-layer stacks into a plurality of differing sized island structures with varying lattice parameters. The plurality of differing sized island structures provide a pattern of varying sized features with varying lattice parameters on the single substrate. A single electron microscopy calibration standard is then fabricated using the pattern of the varying sized features on the single sample. This single electron microscopy calibration standard is thus calibrated for each of the range of magnification settings. The electron microscope may then be calibrated using the single electron microscopy calibration standard.

In a third aspect, the invention is directed to a structure for fabricating an electron microscopy calibration standard. The structure includes a single substrate having first and second layers with a plurality of differing sized island structures with varying lattice parameters comprising a material of a transformation layer over the second layer. This plurality of differing sized island structures provide a pattern of varying sized features with varying lattice parameters on the single substrate. The structure further includes a third layer over portions of the second layer and entirely covering each of the plurality of differing sized island structures with varying lattice parameters, wherein the first layer and each of the plurality of differing sized island structures have varying fringe spacings across the single sample corresponding to a range of magnification settings for the electron microscopy calibration standard.

BRIEF DESCRIPTION OF DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION

Figure 1:
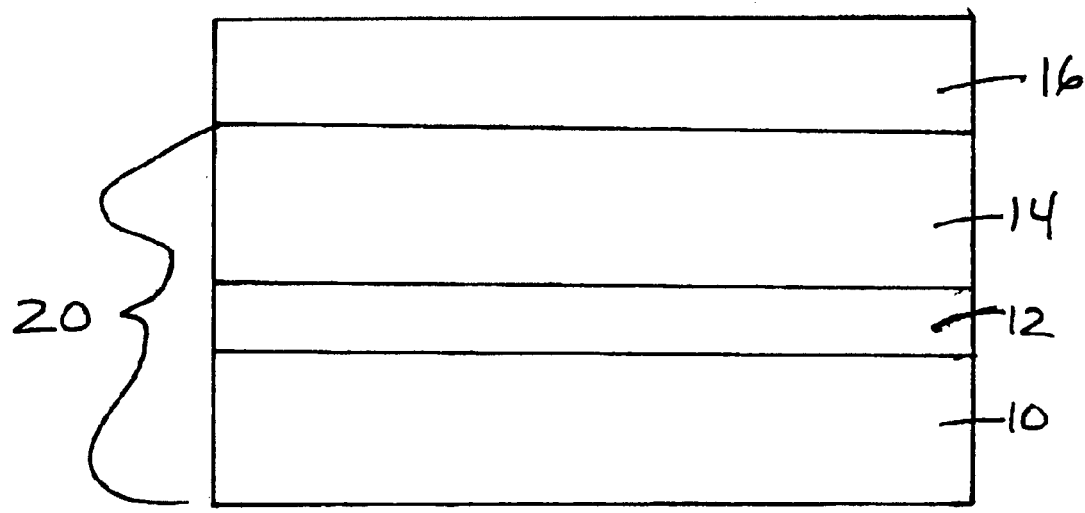
FIG. 1 is a block diagram depicting a cross sectional view of a SIMOX substrate having a transformation layer thereover for use in accordance with the present invention.

In describing the preferred embodiment of the present invention, reference will be made herein to FIGS. 1–6 of the drawings in which like numerals refer to like features of the invention. Features of the invention are not necessarily shown to scale in the drawings.

The present invention is directed to fabricating on a single sample a series of crystalline pairs such that the d-spacing difference between the pairs will generate Moire fringes of the correct spacing(s) to optimally calibrate the magnification settings of an electron microscope over a variety of magnification settings in the range of about 5000× to about 200,000×. Advantageously, this enables high precision calibration of all magnifications in this range in a single sample, as well as effectively and easily tailoring any specific or desired magnification settings within this range on any electron microscope, such as, a scanning transmission electron microscope (STEM), a transmission electron microscope (TEM) and the like. The present invention also advantageously provides a calibration technique and system that enables magnification calibration of a single sample in two orthogonal directions without removing the specimen from the instrument by choosing different imaging conditions in the electron microscope.

Briefly, referring to the drawings depicting the preferred embodiment of the invention, an electron magnification standard is fabricated using a single crystal substrate (20) that is subjected to an oxidation process to form an amorphous compound with the material of the single crystal substrate. This amorphous compound is implanted into the single crystal substrate by known techniques, such as heating, to form a buried amorphous layer (12) that separates the single crystal substrate into a first layer (10) below the amorphous layer and a second layer (14) above the amorphous layer. In so doing, these first and second layers of the single crystal substrate are in exact crystal registry.

Subsequently, a transformation layer (16) is pseudomorphically deposited directly over the second layer. This transformation layer preferably comprises a mixture of a first material and a second material. In the preferred embodiment the transformation layer comprises SiGe. The first material may be the same material as the substrate material (10, 14) and forms a compound with an oxidizing agent in which the second material (Ge) of the transformation layer is substantially insoluble. Further, the second material of the transformation layer must be completely miscible in the substrate material, whereby this mixture follows Vegard's rule.

Once the transformation layer is provided over the second layer of the single crystal substrate, the structure is patterned to form a plurality of bi-layer stacks (14, 16) of different sizes whereby each bi-layer stack comprises the second layer of the single crystal substrate and the transformation layer. The plurality of different sized bilayer stacks are then three dimensionally oxidized using an oxidizing agent to concentrate the second material of the transformation layer into a plurality of island structures (51, 52). In accordance with the invention, the oxidizing agent may include, but is not limited to, oxygen, nitrogen, fluorine, chlorine, silicon bromide, sulfur and the like. During this three dimensional oxidation process, the transformation layer (16) is consumed while sides of the second layer (14) of the single crystal substrate are oxidized to provide a layer (40) entirely over the plurality of different sized island structures. This layer may be a grown layer or a deposited layer that reacts with the transformation layer. As a result, each of the plurality of different sized island structures (51, 52) are in exact crystalline registry with the underlying first substrate layer (10), whereby each island structure has a different concentration of the second material of the transformation layer and a different lattice parameter that are both dependent upon the initial size of the bi-layer stack (14, 16) from which each island structure (51, 52) is fabricated.

Subsequently, a plan view TEM sample is fabricated from the islands and the substrate material to provide Moire patterns in the TEM with spacings dependent upon the lattice constant differences between the substrate and the various islands. The Moire patterns are then used to calibrate the magnification setting of an electron microscope.

The invention will be better understood in accordance with the below detailed description of the preferred embodiment, which relates to TEM, however, it should be understood that the present invention is not limited to the preferred embodiment. A TEM calibration standard sample is initially fabricated by providing a single crystal substrate, which preferably comprises a bulk silicon crystal ingot. This bulk silicon ingot has a crystal plane orientation, which, is established at the beginning of the crystal growth process via the crystal orientation of the seed crystal. Thus, the exact crystal orientation of the substrate being processed is known prior to further processing in accordance with the invention.

In the preferred embodiment, the bulk silicon substrate is processed via separation by implantation of oxygen (SIMOX) to form a SIMOX sample 20. SIMOX involves using high-energy ions to implant a large dose of oxygen ions beneath the surface of a bulk silicon wafer. Upon high-temperature annealing, the implanted oxygen forms a continuous buried oxide layer, or BOX layer, which electrically isolates the Si at the surface, which is, the superficial layer.

Referring to FIG. 1, in processing the bulk silicon substrate by SIMOX, an amorphous layer, i.e., oxygen layer 12 is implanted in very heavy doses into the bulk substrate, beneath the surface thereof, followed by annealing the wafer at a high temperature until a layer of silicon 14 is above the oxygen layer 12 and a layer of silicon 10 is below the oxygen layer 12. Oxygen layer 12 is provided with a thickness ranging from about 10 nm to about 1000 nm, preferably from about 20 nm to about 140 nm. The overlying silicon layer 14 is provided with a thickness ranging from about 10 nm to about 1000 nm, preferably from about 30 nm to about 145 nm.

The resultant SIMOX substrate 20 is preferred as the exact lattice of the crystal orientation of the surface silicon layer 14 and the underlying silicon layer 10 are known and in exact alignment with each other. However, it should be appreciated that any sample, i.e., substrate layering, having at least two crystalline layers that are in exact crystallographic register or alignment may be processed in accordance with the invention.

Once the SIMOX sample 20 is completed, a transformation layer is pseudomorphically deposited directly over the SIMOX substrate. This transformation layer may comprise a material including but not limited to, SiGe. A critical feature of the invention is that the transformation layer comprises a composition that at least includes the substrate material and a material that is miscible in the substrate material. This enables the transformation of the top substrate layer 14 into a buried island within a grown oxide layer, whereby the buried island comprises the material of the transformation layer.

In the preferred embodiment, the transformation layer is a SiGe layer 16 pseudomorphically deposited directly over the SIMOX substrate. The SiGe layer 16 may be deposited over the silicon layer 14 to a thickness ranging from about 10 nm to about 1000 nm, preferably from about 30 nm to about 200 nm, and more preferably to about 60 nm. The SiGe layer 16 has a Ge content ranging from at least about 1% to about 99%, preferably from about 5% to about 25%. This SiGe layer 16 is essential as it enables the transformation of the silicon layer 14 into a buried silicon germanium on insulator (SGOI) island structure, as shown in FIGS. 3A–B, in a subsequent oxidation process as described further below.

Figure 2:
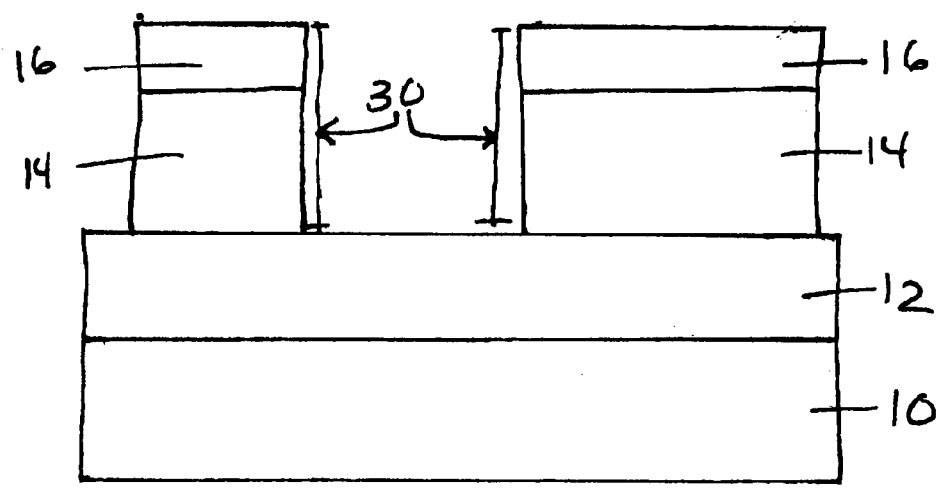
FIG. 2 is a cross sectional view of FIG. 1 illustrating that the sample is patterned and developed so as to form a plurality of bi-layer stacks of differing sizes and/or geometries.

Referring to FIG. 2, the SiGe layer 16 preferably has a planar surface for a patterning. The sample is patterned and developed by known techniques, such as photolithography, to form a plurality of bi-layer stacks, preferably SiGe 16 and silicon 14 bi-layer squares 30. In so doing, as shown in FIG. 2, portions of the underlying oxide layer 12 are exposed. In accordance with the invention, the sizes of the squares are linked to the magnification settings on the transmission electron microscope, and as such, are determined by these magnification settings.

Figure 3A:
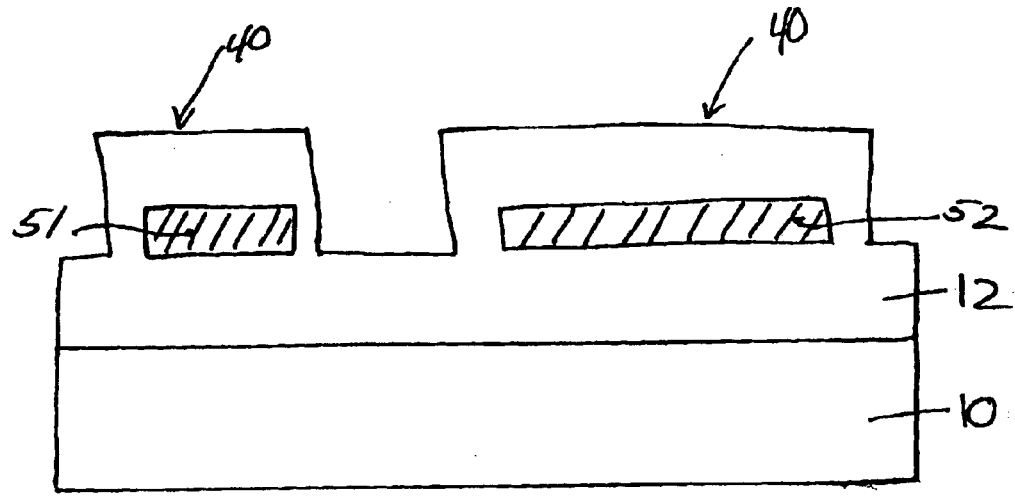
FIG. 3A is a cross sectional view of FIG. 2 illustrating the formation of a variety of different sized islands with differing concentrations of one element of the transformation layer embedded within an insulating layer.
Figure 3B:
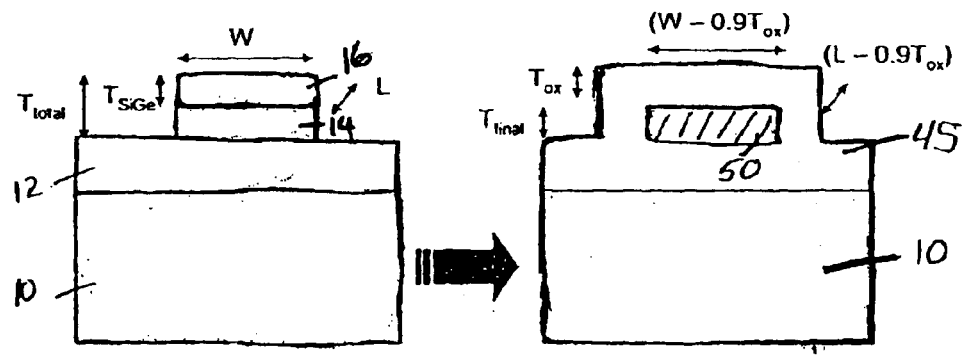
FIG. 3B is a cross sectional view of FIG. 2 illustrating the mechanism of the oxidation process of the preferred embodiment for forming the plurality of island structures on the sample as shown in FIG. 3A.

Once the different sized SiGe 16 and silicon 14 bi-layer squares 30 are formed, the sample is subjected to an oxidation process in order to grow an oxide layer 40 over the sample as shown in the schematics of FIGS. 3A–B. The oxidation step is performed as a three-dimensional oxidation process so that all exposed surface areas of the plurality of different size squares residing over the oxide layer 12 are oxidized in order to form the SGOI island structures, i.e., SiGe islands 50 buried in oxide 45. Oxide 45 is a combination of the grown oxide layer 40 and oxide layer 12.

The oxidation step proceeds at an elevated temperature ranging from about 1000° C. to about 1320° C., preferably greater than about 1150° C., for the purpose of growing oxide layer 40 so as to completely cover the entire SiGe islands 50 as well as portions of the exposed oxide layer 12 and to homogenize the SiGe-Si bilayer. The oxidation process continues at the elevated temperature until homogeneous SGOI island structures are formed below the grown oxide giving the SGOI island structure shown in FIGS. 3A–B. As shown in the schematic drawing of FIG. 3B, during the oxidation process the silicon layer 14 is transformed into a crystalline SiGe layer by Ge segregating into the crystalline Si layer 14 to form the SGOI islands 50, i.e., a SiGe crystal graphic spacers, buried within oxide 45. The elevated temperatures enable such SGOI islands to be formed as single crystal features. Additionally, the germanium content in the SGOI islands 52 may be controlled via changing the thickness of the grown oxide 40 due to rejection of the Ge from the growing oxide layer 40.

The resultant structure comprises a plurality of different sized SGOI islands 50 within the oxide layer 45 on a single sample as shown in FIG. 3A. Preferably, the different sized SGOI islands may have a thickness ranging from about 10 nm to about 2000 nm, more preferably about 35 nm, whereby the SGOI islands have a germanium concentration ranging from at least 1% to about 99%, more preferably from about 5% to about 90%. As a result of the 3-dimensional oxidation process and the segregation of Ge, each of these different sized single crystal SGOI islands on the single substrate has a different germanium content. For example, a sample as shown in FIG. 3A may include a first SGOI island 51 embedded therein having Ge content of about 75% and a second SGOI island 52 embedded therein having Ge content of about 25%.

Thus, in accordance with the invention, the initial step of patterning and developing the substrate to form the plurality of different sized SiGe 16 and silicon 14 bi-layer squares, as shown in FIG. 2, is crucial to the invention as the size of each of these squares determines the size and germanium content of the SGOI islands 50 formed within oxide 45, i.e., below the grown oxide 40 as shown in FIG. 3A. A desired size of the bi-layer stack is calculated based on the desired size of the island(s) 50 to be formed in the sample. That is, the germanium content of each SGOI island 50 is dependent upon the different sizes of the SiGe 16 and silicon 14 bi-layer squares from which each SGOI island is fabricated. As such, the substrate is patterned with a varying pattern across its surface whereby the different sizes of openings in the varying pattern correspond to the plurality of predetermined sizes of the different sized SGOI islands 50 to be formed in the sample.

This varying patterning process of the substrate surface is accomplished by calculating the range of Moire fringe spacings needed to cover the magnification settings which are to be calibrated. The SIMOX substrate is preferred as silicon layers 10, 14 are in exact crystallographic alignment with each other. The varying pattern is then developed to form the plurality of bi-layer stacks corresponding to such predetermined sized SGOI islands 50. Preferably, this varying pattern is determined based on Moire fringe patterns.

Moire fringe patterns are generated under proper imaging conditions using a TEM tool. The sample is viewed in a TEM analytical tool whereby Moire fringe patterns formed between the lower silicon layer 10 and the SiGe layer 52 will have fringe spacings (A) given by the following relation:

$$\Lambda = d_{SiGi} d_{Si} / (d_{SiGi} - d_{Si})$$

wherein, $d_{SiGi}$ and $d_{Si}$ are particular d-spacings respectively for the lower silicon layer 10 and the SiGe layer 52. These fringe spacings depend on the size of the SGOI islands 50 to be formed since the Ge concentration and hence lattice parameters will depend on the island size.

Advantageously, this enables knowing in advance that a magnification within a medium to high magnification range, preferably a range from about 5000× to about 200,000×, can be calibrated to have this desired fringe spacing. That is, the invention enables the fabrication of a series of different sized crystalline pairs on a single sample, whereby the d-spacing difference between these pairs will generate Moire fringes of correct spacings to optimally calibrate the magnification settings of a TEM in the magnification range of 5000× to 200,000×. Therefore, the lattice parameter and the interplanar d-spacings of a given embedded SGOI island in the resultant structure depend on the size of the patterned bi-layer and the germanium concentration in the starting SiGe layer 16.

Figure 4:
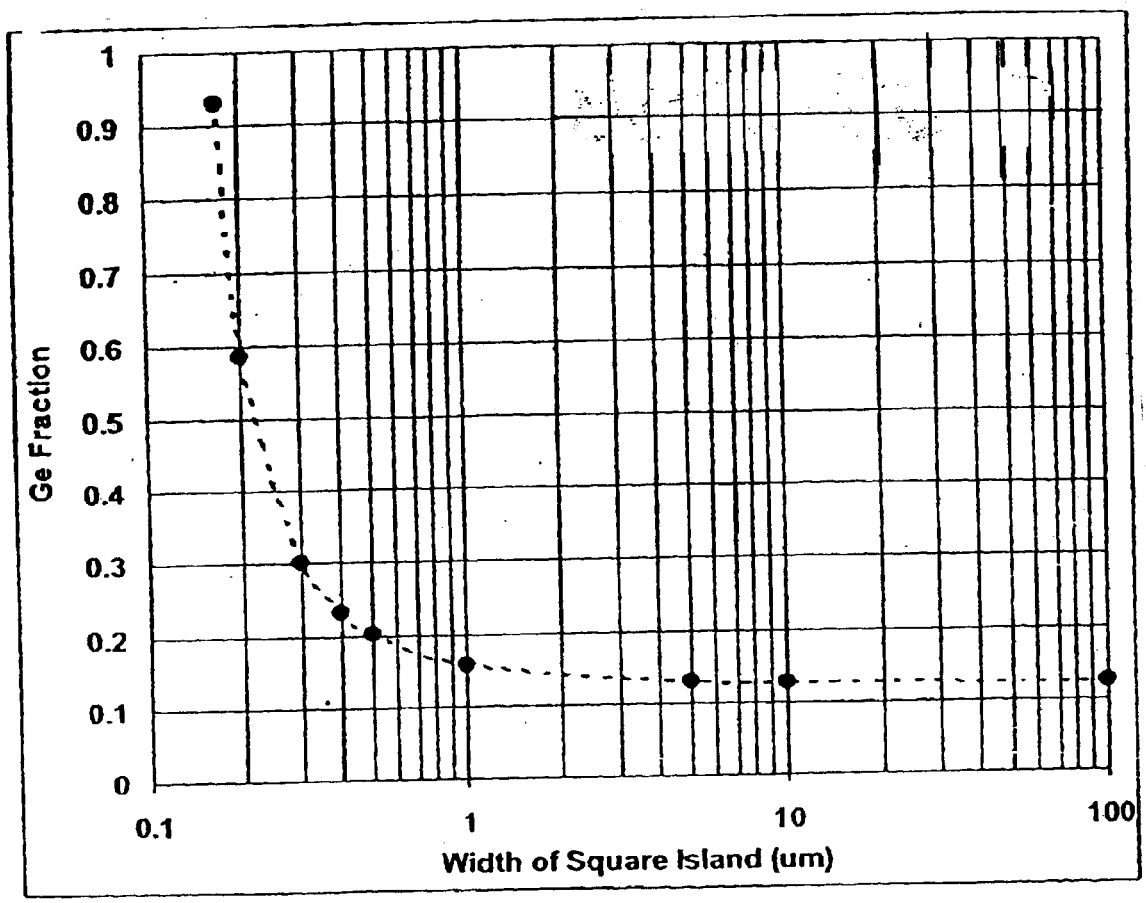
FIG. 4 is a graphical representation in accordance with the preferred embodiment of the invention illustrating that the final germanium concentration of each buried SiGe island varies with the size of each island.
Figure 5:
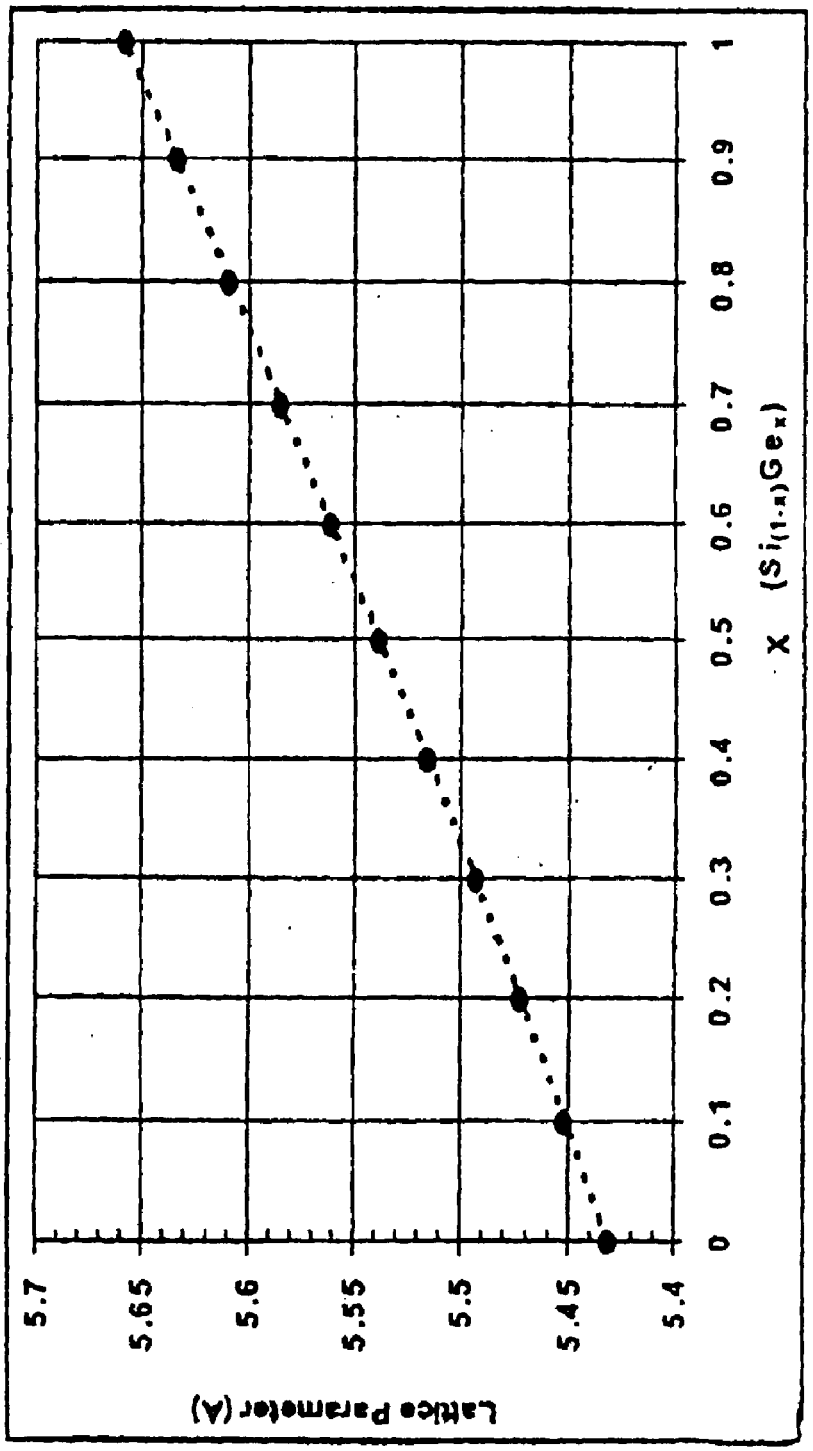
FIG. 5 is a graphical representation in accordance with the preferred embodiment of the invention illustrating that the SiGe lattice parameters vary linearly with the germanium fraction in accordance with the invention.

In accordance with the invention, as the initial bi-layer squares are oxidized from three sides, i.e., a three-dimensional oxidation, the final germanium concentration in the SGOI islands 50 depend on the initial germanium concentration in the pseudomorphically deposited SiGe layer 16 as well as the size of each of the bi-layer squares. For example, the graph of FIG. 4 illustrates the germanium concentrations of the buried SGOI islands 50 on a starting structure of 40 nm of SiGe layer 16 at 13% germanium concentration on a 40 nm silicon layer 14. As shown, the final germanium concentration of each of the buried SGOI islands 50 varies with the size of each island. Further, as depicted in the graphical representation of FIG. 5, the SiGe lattice parameter varies linearly with the germanium fraction.

Once the resultant structure is formed as shown in FIGS. 3A and 3B, the TEM calibration standard is completed by making a TEM plan view calibration sample of the SGOI features. This TEM calibration sample for magnifications ranging from about 5000× to about 200,000× is made using standard polishing and/or focus ion beam techniques.

Figure 6:
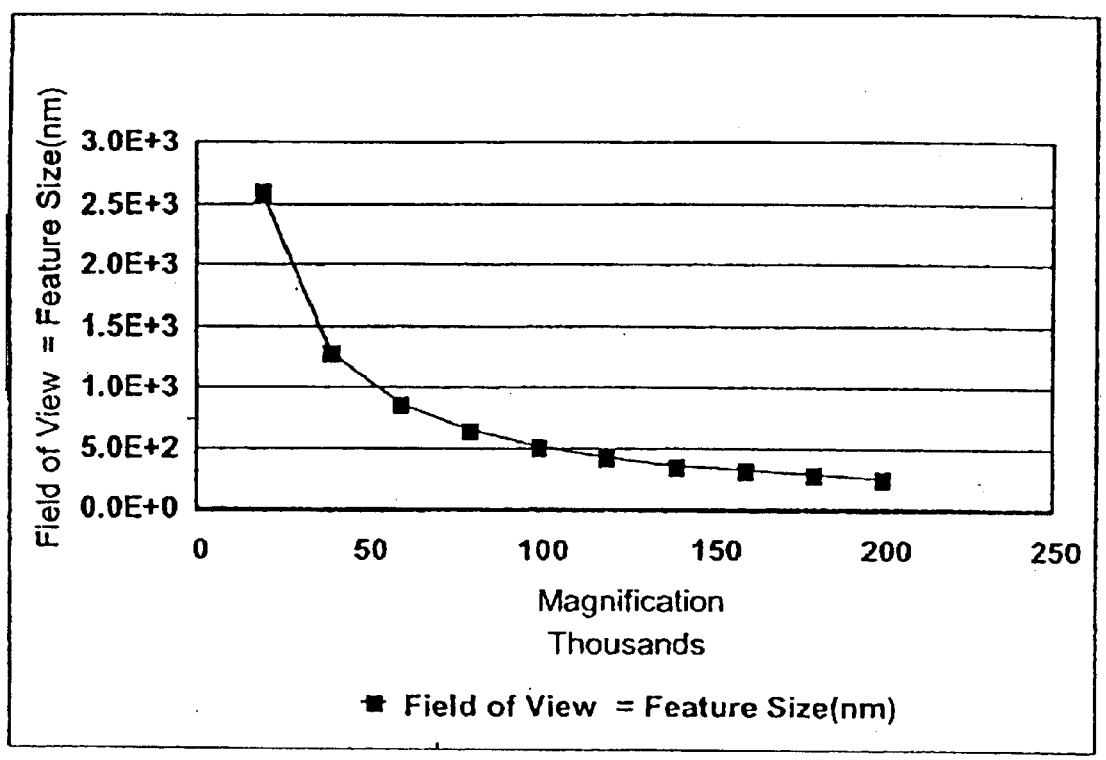
FIG. 6 is a graphical representation in accordance with the preferred embodiment of the invention illustrating the results of an example processed in accordance with the invention for a 60 nm transformation layer with a 17% Ge concentration.

Since the SiGe 52 and silicon 10 layers are mechanically decoupled from each other by the oxide layer 12, the d-spacing differences between such layers are very precise and depend on the lattice parameter of the desired feature size, i.e., SGOI island. The resultant Moire fringe patterns are then used as a ruler to calibrate the magnification settings of the TEM tool by imaging a feature size, which has a spacing that gives a predetermined precision for the field of view imaged. For example, for a 2048×2048 CCD camera, the magnifications can be calibrated to within about 1% accuracy using the feature sizes indicated in the graphical representation as shown in FIG. 6. This graphical representation depicts the results of an example processed in accordance with the invention for a 60 nm transformation layer with a 17% Ge concentration. The graph gives the feature size on the Y-axis necessary to calibrate the magnification on the X-axis to an accuracy of 1%.

Thus, the present invention overcomes the deficiencies in the art by providing a method and system that enables the calibration of all magnification settings of a TEM tool on a single sample. In conventional calibration processes, a certain feature or features on a sample may be sufficient to calibrate one or more (but not all) magnification settings to a given precision as the sizes of such features, in relation to the field of view, are not sufficient to calibrate all settings to the same precision. Thus, in conventional TEM calibration techniques, the sample must be removed from the TEM tool and a different sample having the proper characteristics for the magnification settings in question inserted into the TEM tool and the calibration performed. This process continues until all magnification settings are calibrated, and as such, is cumbersome and introduces random errors in the calibration results.

The present invention overcomes such time consuming and tedious conventional tasks by enabling the fabrication of, on a single sample, a number of different features with different lattice parameters that can be used specifically for each magnification setting of a TEM and whose Moire patterns cover the full field of view for each magnification setting. That is, the present invention advantageously enables the tailoring of Moire fringe spacings, to a desired magnification setting for calibration purposes, by fabricating a series of patterns on a single TEM sample whereby each magnification setting is easily calibrated using a specific SGOI structure, as shown in FIG. 3A, which is selected by a simple x-y translation across the top plan surface of the SGOI structure. The invention eliminates the need for removing calibration samples in and out of the TEM tool, and as such, enables the calibration of low to medium magnification ranges of an electron microscope, preferably magnifications ranging from 5,000× to 200,000×, in a single session.

In accordance with the above description it should be understood that the invention is not limited to TEM or STEM analytical tools. A variety of electron magnification calibration standards can be fabricated using this invention whereby the techniques and systems of the invention may be tailored to desired/selectable magnifications available on a particular analytical electron microscope tool by using a photolithographic mask that gives the correct feature sizes for a given accuracy.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for forming an electron microscopy calibration standard on a single structure comprising:
providing a single substrate having at least a first layer and a second layer in lattice alignment;
depositing a material of a transformation layer over said second layer;
forming a plurality of differing sized bi-layer stacks, each comprising said second layer and said transformation layer;
modifying each of said plurality of bi-layer stacks so as to transform said second layer within each of said differing sized bi-layer stacks into a plurality of differing sized island structures with varying lattice parameters comprising said material of said transformation layer, thereby providing a pattern of varying sized features with varying lattice parameters on said single substrate, and
fabricating an electron microscopy calibration standard of said pattern of said varying sized features on said single substrate.

2. The method of claim 1 further including separating said first and second layers with a buried amorphous layer, said buried amorphous layer mechanically decoupling said first layer from said plurality of differing sized island structures.

3. The method of claim 2 wherein said buried amorphous layer comprises a buried oxide layer, and said step of forming said plurality of differing sized bi-layer stacks comprises exposing said buried oxide layer and growing an oxide layer entirely over said bi-layer stacks and portions of said exposed buried oxide layer to form said plurality of differing sized island structures within said grown oxide and said buried oxide layers.

4. The method of claim 3 wherein said first and second layers comprise a first silicon layer and a second silicon layer in lattice alignment.

5. The method of claim 4 wherein said transformation layer comprises SiGe.

6. The method of claim 1 wherein said step of modifying each of said plurality of bi-layer stacks occurs at an elevated temperature to enable said transformation of said second layer into said plurality of differing sized island structures with varying lattice parameters while simultaneously consuming said transformation layer, said plurality of differing sized island structures being entirely covered with a layer.

7. The method of claim 6 wherein said step of modifying each of said plurality of bi-layer stacks comprises an oxidation process at said elevated temperature ranging from about 1000° C. to about 1320° C.

8. The method of claim 1 wherein each of said plurality of differing sized island structures with varying lattice parameters comprises a single crystal feature.

9. The method of claim 1 wherein said pattern of varying sized features with varying lattice parameters on said single substrate is determined using a Moire fringe spacing that covers each of a magnification setting across a range of magnification settings for said electron microscopy calibration standard to be fabricated from said single substrate.

10. The method of claim 9 wherein said range of magnification settings ranges from 5000× to 200,000×.

11. The method of claim 1 wherein said electron microscopy calibration standard comprises a scanning transmission electron microscope calibration standard or a transmission electron microscope calibration standard.

12. A method for calibrating an electron microscope comprising:
providing an electron microscope having a range of magnification settings;
providing a single substrate having at least a first layer and a second layer in lattice alignment;
depositing a material of a transformation layer over said second layer;
determining a plurality of Moire fringe spacings that cover each magnification setting across said range of magnification settings for said electron microscope; forming a plurality of differing sized bi-layer stacks of said second and transformation layers across said single substrate based on said plurality of Moire fringe spacings;

modifying each of said plurality of bi-layer stacks so as to transform said second layer within each of said differing sized bi-layer stacks into a plurality of differing sized island structures with varying lattice parameters comprising said material of said transformation layer, therein providing a pattern of varying sized features with varying lattice parameters on said single substrate;

fabricating a single electron microscopy calibration standard of said pattern on said single substrate, thereby said single electron microscopy calibration standard being calibrated for each of said range of magnification settings; and calibrating said electron microscope using said single electron microscopy calibration standard.

13. The method of claim 12 wherein said range of magnification settings ranges from 5000× to 200,000×.

14. The method of claim 12 further including separating said first and second layers with a buried amorphous layer, said buried amorphous layer mechanically decoupling said first layer from said plurality of differing sized island structures.

15. The method of claim 14 wherein said buried amorphous layer comprises a buried oxide layer, and said step of forming said plurality of differing sized bi-layer stacks comprises exposing said buried oxide layer and growing an oxide layer entirely over said bi-layer stacks and at least portion of said exposed buried oxide layer to form said plurality of differing sized island structures within said grown oxide and said buried oxide layer.

16. The method of claim 12 wherein said step of modifying each of said plurality of bi-layer stacks occurs an elevated temperature ranging from about 1000° C. to about 1320° C. to enable said transformation of said second layer into said plurality of differing sized island structures with varying lattice parameters.

17. The method of claim 12 wherein said electron microscopy calibration standard comprises a scanning transmission electron microscope calibration standard or a transmission electron microscope calibration standard.

18. A structure for fabricating an electron microscopy calibration standard comprising:

a single substrate having a first layer and a second layer;

a plurality of differing sized island structures with varying lattice parameters comprising a material of a transformation layer over said second layer, said plurality of differing sized island structures providing a pattern of varying sized features with varying lattice parameters on said single substrate and a third layer over portions of said second layer and entirely covering each of said plurality of differing sized island structures with varying lattice parameters, wherein said first layer and each of said plurality of differing sized island structures have varying fringe spacings across said single substrate corresponding to a range of magnification settings for said electron microscopy calibration standard.

19. The structure of claim 18 wherein said material of said plurality of differing sized island structures with varying lattice parameters comprises SiGe.

20. The structure of claim 19 wherein said first layer comprises silicon, said second silicon layer comprises oxide and said third layer comprises grown oxide.

* * * * *